US00PP30878P2

(12) United States Plant Patent
Bacon

(10) Patent No.: US PP30,878 P2
(45) Date of Patent: Sep. 10, 2019

(54) NECTARINE TREE NAMED 'SUNECTWENTYSIX'

(50) Latin Name: ***Prunus persica* var. *nucipersica***
Varietal Denomination: Sunectwentysix

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 15/998,371

(22) Filed: Aug. 10, 2018

(51) Int. Cl.
*A01H 5/08* (2018.01)
*A01H 6/74* (2018.01)

(52) U.S. Cl.
USPC ..... Plt./188

(58) Field of Classification Search
USPC ..... Plt./187, 188, 195
See application file for complete search history.

*Primary Examiner* — Susan McCormick Ewoldt
(74) *Attorney, Agent, or Firm* — Knobbe, Martens, Olson & Bear, LLP

(57) ABSTRACT

A new and distinct nectarine tree variety, *Prunus persica* var. *nucipersica*, cv. 'Sunectwentysix' is characterized by early ripening, very large sized and sweet fruit having a high brix value and a high brix:acid ratio.

1 Drawing Sheet

Latin name of the genus and species claimed: *Prunus persica* var. *nucipersica*.

Variety denomination: 'SUNECTWENTYSIX'.

BACKGROUND AND SUMMARY OF THE INVENTION

This invention relates to the discovery and asexual propagation of a new and distinct variety of nectarine, *Prunus persica* var. *nucipersica* cv. 'Sunectwentysix'. The new variety was first originated by hybridization in June 2014 by Terry Bacon as breeder number: 'NE1674W'. The new variety was first evaluated by Terry A. Bacon near Wasco, Calif. in Kern County.

The new variety 'Sunectwentysix' is characterized by early ripening, very large sized and sweet fruit, a high brix value and a high brix:acid ratio.

The seed parent is 'NE521' (unpatented breeding selection), and the pollen parent is bulk pollen of four unpatented white fleshed nectarines: 'NE1156W'; 'NE1195W'; 'NE1207W'; and 'NE1211W'. The parent varieties were first crossed in February 2011, the date of first sowing being February 2012 and the date of first flowering being February 2014. The new nectarine variety 'Sunectwentysix' was first asexually propagated by Terry Bacon near Wasco, Kern County, Calif. in February 2015 by dormant grafting.

The new variety 'Sunectwentysix' is distinguished from the varieties making up its bulk pollen parent by the flower type, time of full bloom, time of ripening, diameter perpendicular to suture, fruit weight, brix and titratable acidity as compared in the table below.

TABLE 1

| Cultivar | Flower Type | Full Bloom date | First Ripe Date | Diameter perpendicular to suture | Fruit gm | Brix | Titratable Acidity (%) |
|---|---|---|---|---|---|---|---|
| Sunectwentysix | Showy | Feb. 14 | Jun. 5 | 72 mm | 192 | 16 | 0.25 |

TABLE 1-continued

| Cultivar | Flower Type | Full Bloom date | First Ripe Date | Diameter perpendicular to suture | Fruit gm | Brix | Titratable Acidity (%) |
|---|---|---|---|---|---|---|---|
| NE1195W | Showy | Feb. 8 | May 9 | 67 mm | 155 | 15 | 1.0 |
| NE1207W | Non-showy | Feb. 12 | May 16 | 70 mm | 171 | 15 | 0.40 |
| NE1211W | Non-showy | Feb. 8 | May 28 | 70 mm | 184 | 13 | 0.84 |
| NE1156W | Showy | Feb. 6 | Apr. 25 | 55 mm | 80 | 10 | 0.78 |

The new variety 'Sunectwentysix' is distinguished from its seed parent, 'NE521' (unpatented breeding selection), in that the new variety ripens about 33 days later than the seed parent. The new variety 'Sunectwentysix' also has a white flesh color, compared to yellow flesh color for 'NE521'. The new variety 'Sunectwentysix' also has a larger fruit weight of 192 g, higher brix at 16% and Brix:Acid of 64, compared to a fruit weight of 160 g, brix of 13% and Brix:Acid of 14 for 'NE521'.

The new variety 'Sunectwentysix' resembles 'Arctic Sweet' (U.S. Plant Pat. No. 9,542) in that both ripen about the same and both have white flesh. The new variety 'Sunectwentysix' differs from 'Arctic Sweet' in that the new variety has a brix of 16% and Brix:Acid of 64, compared to a brix of 13% and Brix:Acid of 37 for 'Arctic Sweet'. The new variety 'Sunectwentysix' resembles 'Candy Pearl' (U.S. Plant Pat. No. 14,249) in that both have white flesh. The new variety 'Sunectwentysix' differs from 'Candy Pearl' in that the new variety ripens 16 days earlier than 'Candy Pearl'. The new variety 'Sunectwentysix' also differs from 'Arctic Sweet' and 'Candy Pearl' in that the fruit weight of the new variety is 196 g compared to 162 g for 'Arctic Sweet' and 175 g for for 'Candy Pearl'.

The new variety 'Sunectwentysix' has been shown to maintain its distinguishing characteristics through successive asexual propagations by, for example, cuttings and grafting.

BRIEF DESCRIPTION OF THE PHOTOGRAPH

The accompanying color photographic illustration shows typical specimens of the foliage and fruit of the present new nectarine variety 'Sunectwentysix'. The illustration shows the upper and lower surface of the leaves, an exterior and sectional view of a fruit divided across its suture plane to show flesh color, pit cavity and the stone. The photographic illustration was taken shortly after being picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 4 year old 'Sunectwentysix' plants grown in Wasco, Kern County, Calif., and is believed to apply to plants of the variety grown under similar conditions of soil and climate elsewhere. Observations were made in 2017.

TREE

General: (Measurements were taken on 4 year old trees unless otherwise noted.).

- *Size*.—Large. Normal for most nectarine varieties.
- *Spread*.—Normal for most nectarine varieties. Reaches a spread of 5 m with normal vase pruning.
- *Vigor*.—Strong. Approximately 1.8 to 2 meters of growth in the first growing season.
- *Growth*.—Semi-upright.
- *Productivity*.—Very productive, about 800 cartons (25 lbs each) per acre.
- *Bearer*.—Regular.
- *Fertility*.—Self-fertile.
- *Hardiness*.—Hardy in all fruit growing areas of California.
- *Disease resistance/susceptibility*.—No specific testing for relative plant disease resistance/susceptibility has been undertaken. Under close observation in Kern County, Calif., no particular plant/fruit disease resistance/susceptibility has been observed.
- *Chilling requirements*.—About 300 hours at or below 7.2° C.

Trunk: (Measurements were taken at approximately 30 cm above the soil line.).

- *Diameter*.—Approximately 15 cm.
- *Texture*.—Medium shaggy, increasing with age.
- *Trunk color*.—About medium Greyed-Orange 173A becoming darker with age.

Branches: (Measurements were taken at approximately 90 cm above the soil line.).

- *Size*.—Approximately 10 cm.
- *Texture*.—Smooth on young wood, increasing roughness with tree age.
- *Color*.—About medium Greyed-Orange 173A becoming darker with age.
- *Lenticels*.—Present.
- *Lenticels numbers*.—Plentiful.
- *Lenticels density*.—Approximately 12 per $cm^2$.
- *Lenticels color*.—About Light Grey 201D
- *Lenticels length*.—Approximately 3 mm.
- *Lenticels width*.—Approximately 1 mm.

One year old shoots: (Data taken in September at the midpoint of the current-season growth.).

- *Size*.—Average diameter approximately 5 mm.
- *Color*.—Topside: About Dark Greyed-Orange 165A. Underside: About Dark Greyed-Orange 165A.
- *Internode length*.—About 3.0 cm, midway on shoot.
- *Lenticels*.—Plentiful.
- *Lenticels color*.—About Light Grey-Brown 199D.
- *Intensity of anthocyanin on upper side of shoots*.—Medium, more prominent in areas that receive more sunlight.

Vegetative buds: (Data were taken in September at the midpoint of current-season growth.).

- *Position of vegetative bud in relation to shoot*.—Markedly held out.
- *Size*.—Medium, approximately 1.5 mm×2.5 mm.
- *Shape*.—Ovoid.
- *Shape of apex*.—Obtuse.
- *Color*.—About Dark Brown 200B.

Flower buds: (Data were taken in September at the midpoint of current-season growth.).

- *Distribution*.—2 flowers buds per node, on one-year old shoots.
- *Shape*.—Obovate.
- *Dimensions*.—Approximately 4 mm×2.5 mm.
- *Color*.—About Dark Greyed-Orange 165A.
- *Ratio of flower buds to vegetative buds*.—2 flowers buds: 1 vegetative bud.

FOLIAGE

Leaves: (Data taken in June 2018 on fully expanded leaves).

- *Size*.—Medium.
- *Average length*.—Long; approximately 9.0 cm without petiole.
- *Average width*.—Medium; approximately 2.0 cm.
- *Ratio of length to width*.—Very elongated, approximately 4.5:1 ratio.
- *Shape*.—Lanceolate.
- *Color of upper side*.—About Dark Green 139A.
- *Color of lower side*.—About Medium Green 139B.
- *Glossiness of upper side*.—Medium.
- *Angle at apex (excluding tip)*.—Acute.
- *Shape of base*.—Cuneate.
- *Venation*.—Pinately net veined.
- *Vein color*.—About Light Green 139D.
- *Surface texture*.—Smooth.
- *Shape in cross-section*.—Concave.
- *Profile*.—Up-folded.
- *Leaf blade tip*.—Curved downward.
- *Undulation of margin*.—Slight.
- *Density of pubescence of lower side*.—Absent or very sparse.
- *Incisions of margin*.—Crenate.

Petiole:

- *Length*.—Medium; approximately 8 mm.
- *Diameter*.—Approximately 0.7 mm.
- *Color*.—About Light Green 138C.

Stipules:

- *Number/leaf bud*.—Approximately 2 when present.
- *Typical length*.—Medium, approximately 8 mm.

*Color*.—About Dark Greyed-Red 180A.
*Persistence*.—Falls off.

Leaf glands:
*Form*.—Reniform.
*Average number and arrangement*.—0-4, usually 2, arranged nearly parallel on petiole.
*Diameter*.—Approximately 1 mm.
*Color*.—About Dark Greyed-Red 180A when dry.
*Position of nectaries (glands)*.—On the petiole.

FLOWERS

General:
*Time of beginning of flowering*.—Early for the San Joaquin Valley, Calif.
*Flower blooming period*.—First bloom: Approximately February 14 in Wasco, Calif. Location of First bloom: Toward base of tree. Full bloom: Approximately February 18 in Wasco, Calif. Location of Full bloom: Central part of the tree canopy.
*Duration of bloom*.—Approximately 10 days.
*Flower diameter*.—Medium, approximately 4 cm.
*Flower form*.—Showy.

Pedicel:
*Length*.—Long, approximately 10 mm.
*Diameter*.—Approximately 1 mm.
*Color*.—About Dark Greyed-Red 180A when dry.
*Pubescence*.—Absent.

Sepals:
*Number*.—5.
*Length*.—Approximately 6 mm.
*Diameter*.—Approximately 4 mm.
*Shape*.—Triangular.
*Color*.—About Medium Red 44A.
*Texture*.—Smooth to slightly bumpy.
*Margins*.—Smooth.
*Position*.—Adpressed to petals.
*Frequency of flowers with double sepals*.—None.

Receptacle:
*Depth*.—Medium, approximately 2 mm.
*Pubescence of inner surface*.—Absent.
*Pubescence of outer surface*.—Absent.

Petals:
*Number*.—5.
*Arrangement*.—Slightly overlapping.
*Color of upper and lower surfaces*.—About Medium Red-Purple 62C.
*Surface texture*.—Smooth.
*Length*.—Long, approximately 18 mm.
*Width*.—Approximately 15 mm.
*Shape*.—Circular.
*Apex shape*.—Rounded.
*Base shape*.—Narrow at point of attachment.
*Undulation of margin*.—Medium.
*Frequency of flowers with double petals*.—None.

Pistil:
*Length*.—Approximately 37 mm.
*Ovary diameter*.—Approximately 1.5 mm.
*Pubescence*.—Absent.
*Stigma extension in comparison to anthers*.—Above.
*Frequency of supplementary pistils*.—Few.

Stamens:
*Number*.—Approximately 32-38. Average 34.
*Length*.—Variable, ranging approximately from 3 mm to 10 mm.
*Filament color*.—About White 155A.
*Pollen color*.—About Medium Red 52A.
*Position*.—Perigynous.

FRUIT

General: (Description taken near Wasco, Kern County, Calif.).
*Time of beginning of fruit ripening*.—Early for the San Joaquin Valley, Calif.
*Harvest*.—
*Date of first pick*.—Approximately June 5.
*Date of last pick*.—Approximately June 14.

Maturity when described: Firm-mature.

Size:
*Average size*.—Very large.
*Diameter in line with suture plane*.—Approximately 70 mm.
*Diameter perpendicular to suture*.—Broad, approximately 72 mm.
*Average weight*.—Approximately 192 gm.
*Height*.—Tall, approximately 75 mm.

Shape:
*Viewed from apex*.—Circular.
*In lateral view, perpendicular to suture*.—Circular.
*In-line with suture*.—Circular.
*Symmetry*.—Symmetric or slightly asymmetric.
*Shape of base*.—Slightly depressed.
*Shape of apex*.—Rounded.
*Depth of stalk cavity*.—Medium, approximately 10 mm.
*Width of stalk cavity*.—Medium, approximately 10 mm.
*Depth of suture*.—Absent or very shallow.

Skin:
*Thickness*.—Medium, typical of most varieties.
*Adherence to flesh*.—Strong.
*Surface texture*.—Nearly smooth.
*Taste*.—Neutral.
*Reticulation*.—Absent.
*Tendency to crack*.—Rare.
*Pubescence*.—Absent.
*Bloom on skin*.—Absent or very week.
*Ground color*.—About White 155A.
*Relative area of over color of skin*.—Nearly whole surface.
*Overcolor*.—About Dark Red, ranging from Dark Red 53C to Dark Red 53A.
*Pattern of over color of skin*.—Solid.
*Number of lenticels*.—Few, variable from 2 to 28 per $cm^2$.
*Size of lenticels*.—Very small, approximately less than 0.3 mm.

Flesh:
*Ripens*.—Evenly.
*Texture*.—Slow-softening, non-melting, firm-juicy.
*Color*.—About White 155A.
*Flavor*.—Sweet, subacid/low-acid.
*Firmness*.—Firm.
*Juiciness*.—Medium, able to squeeze free juice easily.
*Acidity*.—Low for nectarines, 0.25% titratable acidity.
*Sweetness*.—High.
*Brix*.—Approximately 16% at harvest.
*Adherence of stone to flesh*.—Adherent.
*Fiber*.—Medium.

Stone:

*Stone freeness*.—Clings.

*Stone size*.—Size: Medium. Length: Approximately 12 mm. Diameter in line with suture: Approximately 10 mm. Diameter perpendicular to suture: Approximately 10 mm.

*Color*.—About Light Greyed-Orange 164C.

*Position of maximum diameter*.—Middle.

*Stone shape*.—Lateral view: Medium elliptic. Basal view: Broad elliptic. Ventral view: Broad elliptic.

*Base shape*.—Nearly straight.

*Apex shape*.—Pointed.

*Ridges*.—Rounded throughout.

*Outgrowing keel*.—Well developed.

*Ventrical edge*.—Medium.

*Dorsal edge*.—Full, deep grooves.

*Fibers*.—Retains short fiber-like threads along ridges.

*Symmetry in lateral view*.—Symmetric.

*Texture of lateral surface*.—Rough.

*Width of stalk-end*.—Medium, approximately 4 mm.

*Tendency to split*.—Rare.

What is claimed is:

1. A new and distinct nectarine tree as herein described and illustrated.

* * * * *

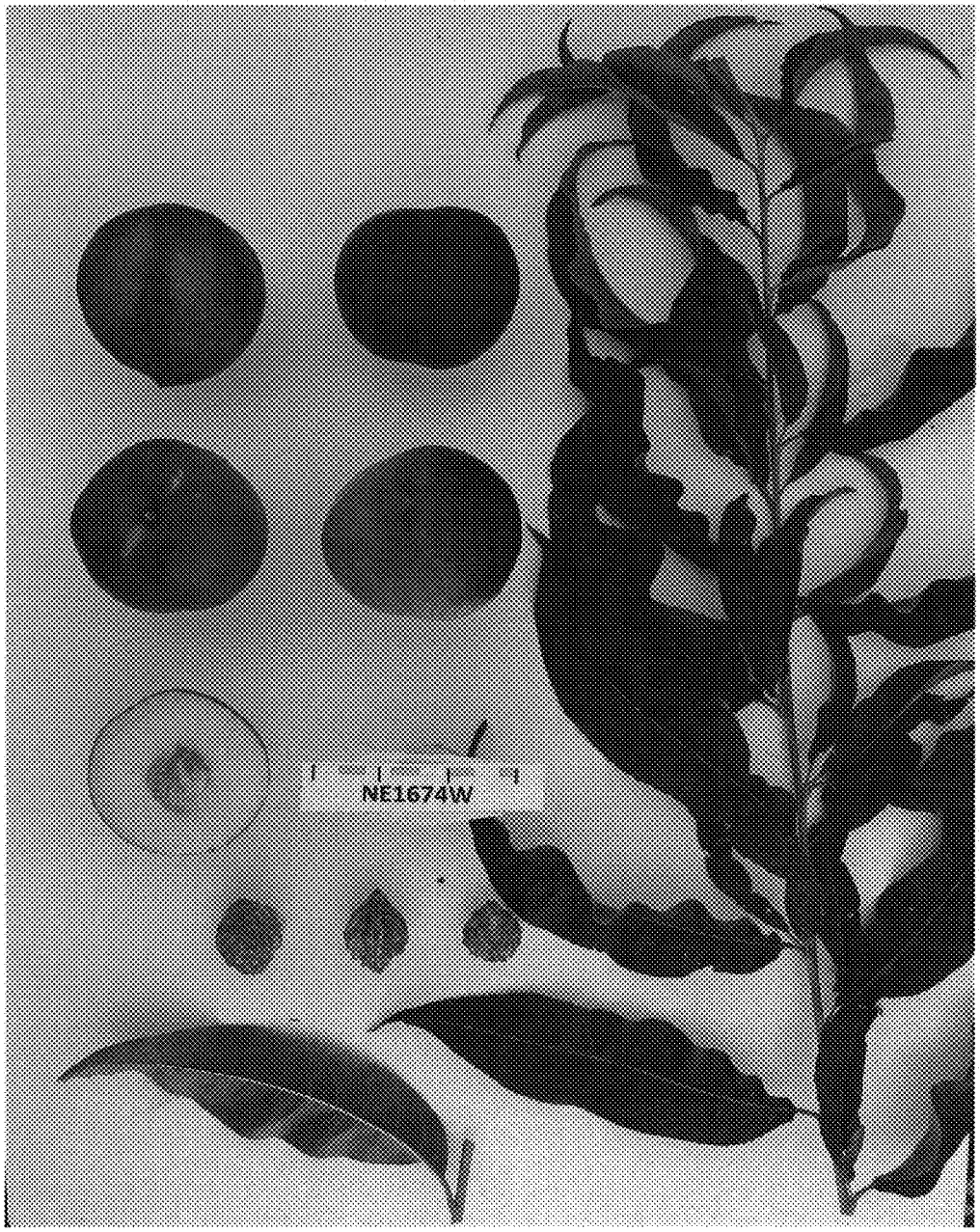
NE1674W